(12) United States Patent
McCrink et al.

(10) Patent No.: US 8,557,236 B2
(45) Date of Patent: Oct. 15, 2013

(54) CARDIOVASCULAR SUPPORT SUPPLEMENT AND COMPOSITIONS AND METHODS THEREOF

(75) Inventors: Thomas J McCrink, Brielle, NJ (US); Peter Marino, Brick, NJ (US)

(73) Assignee: Vascure Natural LLC, Brielle, NJ (US)

( * ) Notice: Subject to any disclaimer, the term of this patent is extended or adjusted under 35 U.S.C. 154(b) by 24 days.

(21) Appl. No.: 13/024,034

(22) Filed: Feb. 9, 2011

(65) Prior Publication Data

US 2011/0195058 A1    Aug. 11, 2011

Related U.S. Application Data

(60) Provisional application No. 61/302,654, filed on Feb. 9, 2010.

(51) Int. Cl.
*A61K 38/43*    (2006.01)

(52) U.S. Cl.
USPC ........................................ 424/94.1

(58) Field of Classification Search
None
See application file for complete search history.

(56) References Cited

U.S. PATENT DOCUMENTS

| 5,316,765 A | 5/1994 | Folkers et al. |
| 2002/0058026 A1 | 5/2002 | Hammerly |
| 2005/0267197 A1 | 12/2005 | Berlin |
| 2006/0003947 A1 * | 1/2006 | Udell ............................. 514/26 |
| 2006/0058283 A1 | 3/2006 | Lipshutz |
| 2007/0253941 A1 | 11/2007 | Naidu et al. |
| 2008/0089876 A1 | 4/2008 | Cavazza |
| 2008/0305095 A1 * | 12/2008 | Karl ............................. 424/94.1 |
| 2010/0144665 A1 | 6/2010 | Linnane |

FOREIGN PATENT DOCUMENTS

| EP | 0383432 A1 | 8/1990 |
| EP | 1251834 A1 | 10/2002 |

OTHER PUBLICATIONS

Mandy Wyman, "Coenzyme Q10: A therapy for hypertension and statin-induced myalgia?," Cleveland Clinic Journal of Medicine, Jul. 2010, vol. 77 (7), pp. 435-442, 6 pages.

Peter H. Langsjoen et al., "The clinical use of HMG CoA-reductase inhibitors and the associated depletion of coenzyme $Q_{10}$. A review of animal and human publications," BioFactors, 2003, vol. 18, No. 1-4, 1 page.

Ken R. Wells, "Vitamin Q10 (Coenzyme Q10)," EnCognitive.com, retrieved at http://www.encognitive.com/node/1166, date of retrieval May 1, 2013, 5 pages.

* cited by examiner

*Primary Examiner* — Allison Ford
*Assistant Examiner* — Yvonne Pyla
(74) *Attorney, Agent, or Firm* — Kacvinsky Daisak PLLC; John Maldjian, Esq.; Alexander D. Walter, Esq.

(57) ABSTRACT

A cardiovascular support composition is provided comprising red yeast rice, Coenzyme-Q10, and phytosterols. A method for maintaining cardiovascular health is also provided comprising administering the composition comprising red yeast rice, Coenzyme-Q10, and phytosterols in a predefined dosage to an individual in need thereof.

19 Claims, No Drawings

CARDIOVASCULAR SUPPORT SUPPLEMENT AND COMPOSITIONS AND METHODS THEREOF

CROSS-REFERENCE TO RELATED APPLICATIONS

This application claims priority to, and the benefit of, pending U.S. Provisional Application Ser. No. 61/302,654, filed Feb. 9, 2010, entitled "Cardiovascular Support Supplement and Compositions and Methods Thereof," the disclosure of which is incorporated herein by reference in its entirety.

BACKGROUND

1. Field of the Invention

Embodiments of the present invention generally relate to cardiovascular support supplements and compositions and methods thereof. More specifically, embodiments of the present invention relate to a cardiovascular support supplement and compositions and methods for using these supplements and compositions for prophylactic nutritional supplementation and therapeutic nutritional supplementation in, for example, cardiovascular conditions.

2. Description of the Related Art

Cardiovascular disease remains the highest cause of death in the developed countries. In the United States alone, cardiovascular disease accounts for more than one-third of all deaths. Current estimates show more than 81 million Americans currently live with one or more types of cardiovascular disease, and about 1.7 million suffer from heart attack or stroke annually. The direct and indirect cost in the United States of cardiovascular disease is estimated to be more than 500 billion dollars annually.

Various organizations and health professionals have proposed primary prevention strategies that involve pharmaceutical solutions, interventional cardiology, and changes in diet and lifestyle. Although these recommendations appear rational, they have not had any significant impact in reducing the risk of heart disease. This would suggest that despite advances in pharmaceuticals, interventional cardiology, diet and lifestyle education, there are factors involved in the development of cardiovascular disease currently not being addressed.

Thus, there is a need for an improved cardiovascular support supplement and compositions and methods thereof.

SUMMARY

Embodiments of the present invention provide supplements, compositions and methods of using these compositions for both prophylactic and therapeutic nutritional supplementation, specifically related to cardiovascular health.

Specifically, for example, embodiments of the present invention relate to novel compositions of nutrients that can be used to supplement the nutritional deficiencies observed in patients with a diagnosis of high cholesterol or a propensity or disposition to high cholesterol.

In one embodiment, there is provided a cardiovascular support composition comprising red yeast rice, Coenzyme-Q10, and phytosterols. In at least one embodiment, there is provided a method for maintaining cardiovascular health comprising administering the composition comprising red yeast rice, Coenzyme-Q10, and phytosterols in a predefined dosage to an individual in need thereof.

In at least one embodiment, compositions of the present invention may comprise one or more of about 10 mg to about 450 mg of Coenzyme-Q10; about 100 mg to about 2400 mg of red yeast rice; about 100 mg to about 2400 mg of phytosterols; and at least one or more excipients. In at least one embodiment, the form of the compositions of the present invention may be selected from the group consisting of a pill, a tablet, a caplet, a capsule, powder, a suspension, and a gel.

In at least one embodiment, the compositions of the present invention may comprise one or more of red yeast rice, Coenzyme-Q10, phytosterols and Omega-3 fish oil. In at least one embodiment, the compositions of the present invention may comprise one or more of about 10 mg to about 450 mg Coenzyme-Q10, from about 100 mg to about 2400 mg red yeast rice, and from about 100 mg to about 2400 mg phytosterols. In at least one embodiment, the compositions of the present invention may comprise one or more of about 230 mg Coenzyme-Q10, from about 1250 mg red yeast rice, and from about 1250 mg phytosterols.

In at least one embodiment, the compositions of the present invention may comprise one or more of from about 5% to about 25% Coenzyme-Q10 by weight, from about 35% to about 55% red yeast rice by weight, and from about 35% to about 55% phytosterols by weight. In at least one embodiment, the compositions of the present invention may comprise one or more of from about 15% Coenzyme-Q10 by weight, from about 42% red yeast rice by weight, and from about 43% phytosterols by weight.

In at least one embodiment, the compositions of the present invention may comprise one or more of dicalcium phosphate, microcrystalline cellulose, stearic acid, croscarmellose sodium, magnesium trisillicate, magnesium stearate, or hydroxypropyl methylcellulose.

In at least one embodiment, the compositions of the present invention may comprise one or more flavors. In at least one embodiment, the compositions of the present invention may comprise one or more coloring agents. In at least one embodiment, the compositions of the present invention may comprise one or more spices. In at least one embodiment, the compositions of the present invention may comprise one or more emulsifiers. In at least one embodiment, the compositions of the present invention may comprise one or more emulsifiers comprising at least of lecithin, mono-n dye-glycerides, or combinations thereof. In at least one embodiment, the compositions of the present invention may comprise one or more of a pill, a tablet, a caplet, a capsule, powder, a suspension, and a gel.

In at least one embodiment, the compositions of the present invention may comprise one or more of at least one carrier selected from the group consisting of water, milk, juice, soda, starch, vegetable oil, salt solution, hydroxymethyl cellulose, or carbohydrates.

In an embodiment, the methods of the present invention may utilize the compositions of the present invention suitable for administration to subjects with a diagnosis of high cholesterol or a propensity or disposition to high cholesterol. The methods of the present invention may be directed to the alleviation of nutritional deficiencies resulting from such diagnosis of high cholesterol or a propensity or disposition to high cholesterol.

In one embodiment, the methods of the present invention may utilize compositions comprising one or more of red yeast rice; Coenzyme-Q10; and phytosterols wherein the predefined dosage is administered over a predetermined time interval. In at least one embodiment, the compositions of the present invention may comprise one or more of about 10 mg to about 450 mg of Coenzyme-Q10; about 100 mg to about 2400 mg of red yeast rice; about 100 mg to about 2400 mg of phytosterols; at least one or more excipients; and wherein the form of the composition is selected from the group consisting of a pill, a tablet, a caplet, a capsule, powder, a suspension, and a gel. In at least one embodiment, the compositions of the present invention may further comprise Omega-3 fish oil.

In at least one embodiment, the compositions of the present invention may comprise one or more of dicalcium phosphate, microcrystalline cellulose, stearic acid, croscarmellose sodium, magnesium trisillicate, magnesium stearate, or hydroxypropyl methylcellulose. In at least one embodiment, the compositions of the present invention may comprise one or more emulsifiers. In at least one embodiment, the compositions of the present invention may comprise one or more emulsifiers, wherein the one or more emulsifiers may comprise at least one of lecithin, mono-n dye-glycerides, or combinations thereof.

In at least one embodiment, the compositions of the present invention may comprise one or more of at least one or more flavors, at least one or more coloring agents, or at least one or more spices. In at least one embodiment, the compositions of the present invention may comprise one or more carriers selected from the group consisting of water, milk, juice, soda, starch, vegetable oil, salt solution, hydroxymethyl cellulose, or carbohydrates.

DETAILED DESCRIPTION

So the manner in which above recited features of the present invention can be understood in detail, a more particular description of embodiments of the present invention, briefly summarized above, may be had by reference to embodiments, several of which are described in the detailed description. The detailed description includes examples. As such, the detailed description is not to be considered limiting, and other equally effective examples are possible and likely.

Embodiments of the present invention relate to a cardiovascular support supplement and compositions and methods thereof. Generally, embodiments of the composition contain at least one ingredient from each of the following compounds: red yeast rice, Coenzyme Q10 ("CoQ10"), and phytosterols. Simultaneous delivery of these compounds generally allows for synergistic effects and overall promotion of cardiovascular and vascular health. More specifically, simultaneous delivery of these compounds may generally provide health benefits that include, but are not limited to, providing antioxidants that support a healthy inflammatory response, reducing free radical damage, supporting healthy triglyceride and cholesterol levels, and promoting arterial integrity.

An exemplary cardiovascular support supplement may comprise, for example, a single caplet comprising a composition of red yeast rice, CoQ10, and phytosterols. When administered in an optimal strength, the exemplary cardiovascular support supplement may support healthy cholesterol levels while reducing the cost of purchasing red yeast rice, CoQ10, and phytosterols separately by making it available in a single caplet. Administering red yeast rice, CoQ10, and phytosterols in a single caplet may also improve patient compliance because instead of having to take three capsules, a patient may only have to take a single capsule and the burden of taking the supplements would be decreased. The patient may also be able to more easily take the correct dosages. The cardiovascular support supplement may offer synergistic benefits by the simultaneous delivery of red yeast rice, CoQ10, and phytosterols.

Generally, red yeast rice is fermented rice and is cultivated with the mold Monascus purpureus. Further, the mold provides a reddish purple color to the red yeast rice. Various living organisms include CoQ10, which is used for production of cellular energy. Further, CoQ10 may be soluble in fat. Pytosterols may comprise steroid alcohols that can be available naturally in plants.

The cardiovascular support supplement may comprise red yeast rice, CoQ10 and pytosterols. Alternatively, the composition may include or be used in combination with Omega-3 Fish Oil. The combination may supply a source of important nutritionally essential n-3 fatty acids such as Eicosapentaenoic Acid (EPA) and Docosahexaenoic Acid (DHA) to an individual. The individual may be, for example, a patient suffering from heart disease. Further, the combination may support healthy triglyceride levels, and may reduce the risk of heart disease.

In another embodiment of the present invention, the cardiovascular support supplement may include or be used in combination with vitamin D3. The combination of the cardiovascular support supplement with vitamin D3 may provide additional benefits such as, but not limited to, increased bone strength, increased immune function, and increased inflammatory response. In yet another embodiment, the composition may be used in combination with Omega-3 fish oil and vitamin D3 for achieving the aforementioned benefits. The cardiovascular support supplement of the embodiments disclosed herein may be utilized as an alternative or a supplement to current pharmaceutical and interventional forms of treatment of cardiovascular diseases.

In many embodiments of the present invention, the cardiovascular support supplement comprises between about 100 mg to about 2400 mg of red yeast rice, between about 10 mg to about 450 mg of CoQ10, and between about 100 mg to about 2400 mg of phytosterols.

In one embodiment of the present invention, the cardiovascular support supplement may comprise between about 300 mg to about 1800 mg of red yeast rice. In another embodiment of the present invention, the cardiovascular support supplement may comprise between about 50 mg to about 300 mg of CoQ10. In yet another embodiment of the present invention, the cardiovascular support supplement may comprise between about 300 mg to about 1800 mg of phytosterols.

In one embodiment of the present invention, the cardiovascular support supplement may comprise between about 35% to about 55% by weight of red yeast rice. In another embodiment of the present invention, the cardiovascular support supplement may comprise between about 5% to about 25% by weight of CoQ10. In yet another embodiment of the present invention, the cardiovascular support supplement may comprise between about 35% to about 55% by weight of phytosterols.

In one particular embodiment of the present invention, a cardiovascular support supplement comprises about 600 mg of red yeast rice, about 100 mg of CoQ10, and about 600 mg of phytosterols. In an alternative embodiment of the present invention, a cardiovascular support supplement comprises about 1200 mg of red yeast rice, 200 mg of CoQ10, and 1200 mg of phytosterols. In yet another alternative embodiment of the present invention, a cardiovascular support supplement comprises 1800 mg of red yeast rice, 300 mg of CoQ10, and 1800 mg of phytosterols.

While the above elements comprise the essential vitamins, minerals and nutrients of embodiments of the present invention, the cardiovascular support supplement can also contain other ingredients, provided such ingredients do not materially or substantially alter the embodiments of the present invention.

In many embodiments of the present invention, the cardiovascular support supplement may further comprise one or more excipients. The excipients may be inactive ingredients that can be used as carriers for the active ingredients of the formulation. Examples of excipients include, but are not limited to, dicalcium phosphate, microcrystalline cellulose, stearic acid, croscarmellose sodium, magnesium trisillicate, magnesium stearate, hydroxypropyl methylcellulose, and so forth. In addition to excipients, other inactive ingredients may also be provided, such as flavoring agents, coloring agents, spices, and so forth. The amount of the other inactive ingredients per unit of the cardiovascular support supplement may be selected based on the total number of unit servings of the cardiovascular support supplement administered to a patient. Moreover, the total amount of the other ingredients may also be selected, in part, based on the health condition of the patient.

The flavorings can be in the form of flavored extracts, volatile oils, chocolate flavorings (e.g., non-caffeinated cocoa or chocolate or chocolate substitute such as carob), peanut butter flavoring, cookie crumbs, crisp rice, vanilla or any commercially available flavoring. Moreover, flavoring can be protected with mixed tocopherols. Examples of flavorings include, but are not limited to, pure anise extract, imitation banana extract, imitation cherry extract, chocolate extract, pure lemon extract, pure orange extract, pure peppermint extract, imitation pineapple extract, imitation rum extract, imitation strawberry extract, or pure vanilla extract or volatile oils, such as balm oil, bay oil or bergamots oil, cedar-wood oil, cherry oil, walnut oil, cinnamon oil, clove oil, or peppermint oil, peanut butter, chocolate flavoring, vanilla cookie crumb, butterscotch or toffee, and so forth.

In many embodiments of the present invention, emulsifiers may be added for stability of the cardiovascular support supplement. Examples of emulsifiers include, but are not limited to, lecithin (e.g., from egg or soy), and/or mono-n dye-glycerides. Other emulsifiers are readily apparent to the skilled artesian and selection of suitable emulsifiers may depend, in part, on the formulation of the cardiovascular support supplement.

The cardiovascular support supplement of embodiments of the present invention may be formulated using any pharmaceutically acceptable forms of the vitamins, minerals and other nutrients discussed above, including their salts. For example, the cardiovascular support supplement may be formulated into pills, tablets, caplets, capsules, tablets, powders, suspensions, gels or liquids, optionally comprising an acceptable carrier such as but not limited to water, milk, juice, sodas, starch, vegetable oils, salt solutions, hydroxymethyl cellulose, carbohydrates, and so forth. In one embodiment of the present invention, the cardiovascular support supplement may be formulated with foods or liquids. Examples of foods or liquids include, but are not limited to, a single serving bar or beverage. In an embodiment of the present invention, the ingredients or the cardiovascular support supplement may be dried and made readily soluble in water and other consumable liquids as described above.

In accordance with embodiments of the present invention, a method for providing cardiovascular support may comprise administering the cardiovascular support supplement in a predefined dosage. Further, the cardiovascular support supplement may be administered at least once during a predetermined time interval, for example, per hour, per day, per week, and so forth. In one embodiment of the present invention, the predefined dosage may include about 600 mg of red yeast rice, about 100 mg of CoQ10, and about 600 mg of phytosterols, and may be administered to the patient, twice a day, every day over a predetermined time duration (for example, days, weeks, or months).

EXAMPLE

A study is undertaken to evaluate the effectiveness of embodiments of the present invention in the treatment of patients. The objective of the study is to determine whether oral intake of an embodiment composition results in an improvement of cardiovascular health of the patient, either therapeutically or prophylacticly.

A study is conducted over a 6 month period. A total of 25 patients aged 18 to 75 years, with a diagnosis of high cholesterol or a propensity or disposition to high cholesterol are chosen for the study. An initial assessment of cardiovascular health status is conducted utilizing methods such as a baseline blood test.

Patient A is administered daily 4 single caplets comprising a composition of about 600 mg of red yeast rice, about 100 mg of CoQ10, and about 600 mg of phytosterols; and a single caplet of a statin. Patient B is administered daily 4 single caplets comprising a composition of about 600 mg of red yeast rice, about 100 mg of CoQ10, and about 600 mg of phytosterols; and a single caplet of a statin. Patient C is administered daily 4 single caplets comprising a composition of 600 mg of red yeast rice, about 100 mg of CoQ10, and about 600 mg of phytosterols; and a single caplet of statin. Patient D is administered daily 4 single caplets comprising a composition of about 600 mg of red yeast rice, about 100 mg of CoQ10, and about 600 mg of phytosterols. Patient E is administered daily 4 single caplets comprising a composition of about 600 mg of red yeast rice, about 100 mg of CoQ10, and about 600 mg of phytosterols. Patient F is administered daily 4 single caplets comprising a composition of about 600 mg of red yeast rice, about 100 mg of CoQ10, and about 600 mg of phytosterols. Patient G is administered daily 4 single caplets comprising a composition of about 600 mg of red yeast rice, about 100 mg of CoQ10, and about 600 mg of phytosterols. The exemplary results of a study conducted with administration of the cardiovascular support supplement to multiple patients with different cholesterol levels are illustrated below:

Patient A: total cholesterol was reduced from about 350 to about 159 and Low-Density Lipoprotein (LDL) cholesterol for reduced from about 250 to about 79. Further, the patient A was on combination therapy (administering daily 4 single caplets comprising a composition of about 600 mg of red yeast rice, about 100 mg of CoQ10, and about 600 mg of phytosterols; and a single caplet of statin), but discontinued statin use due to side effects.

Patient B: LDL was reduced from 98 to 84. Although, the reduction may seem low as compared to Patient A, it is well known that it is more difficult to reduce lower level of cholesterol to an even lower level. Further, Patient B, had a hereditary disorder causing cholesterol to be very high.

Patient C: LDL was reduced from 120 to 96.
Patient D: LDL was reduced from 144 to 102.
Patient E: LDL was reduced from 197 to 93.
Patient F: LDL was reduced from 156 to 96.
Patient G: LDL was reduced from 170 to 100.

A significant improvement in cardiovascular health status is observed in the treated subjects upon completion of the study. The study confirms that oral administration of the composition of the present composition is effective as a nutritional supplement, either therapeutically or prophylacticly, for example, in preventing the severity or delaying or preventing the onset of high cholesterol.

While the foregoing is directed to embodiments of the present disclosure, other and further embodiments of the invention may be devised without departing from the basic scope thereof. It is understood that various embodiments described herein may be utilized in combination with any other embodiment described, without departing from the scope contained herein. Further, the foregoing description is not intended to be exhaustive or to limit the invention to the precise form disclosed. Modifications and variations are possible in light of the above teachings or may be acquired from practice of the invention.

No element, act, or instruction used in the description of the present application should be construed as critical or essential to the invention unless explicitly described as such. Also, as used herein, the article "a" is intended to include one or more items. Where only one item is intended, the term "one" or similar language is used. Further, the terms "any of" followed by a listing of a plurality of items and/or a plurality of categories of items, as used herein, are intended to include "any of," "any combination of," "any multiple of," and/or "any combination of multiples of" the items and/or the categories of items, individually or in conjunction with other items and/or other categories of items. Further, as used herein, the term "set" is intended to include any number of items, including zero. Further, as used herein, the term "number" is intended to include any number, including zero.

Moreover, the claims should not be read as limited to the described order or elements unless stated to that effect. In addition, use of the term "means" in any claim is intended to invoke 35 U.S.C. §112, ¶ 6, and any claim without the word "means" is not so intended.

What is claimed is:

1. A composition for cardiovascular support, comprising active ingredients consisting of red yeast rice, Coenzyme-Q10, and phytosterols.

2. A composition for cardiovascular support comprising active ingredients consisting of red yeast rice, Coenzyme-Q10, phytosterols and Omega-3 fish oil.

3. The composition of claim 1, wherein the Coenzyme-Q10 comprises about 10 mg to about 450 mg, the red yeast rice comprises from about 100 mg to about 2400 mg, and the phytosterols comprise from about 100 mg to about 2400 mg.

4. The composition of claim 1, wherein the Coenzyme-Q10 comprises about 220 mg, the red yeast rice comprises about 1250 mg, and the phytosterols comprise about 1250 mg.

5. The composition of claim 1, wherein the amount of Coenzyme-Q10 comprises from about 5% to about 25% by weight of active ingredients, the amount of red yeast rice comprises from about 35% to about 55% by weight of active ingredients, and the amount of phytosterols comprises from about 35% to about 55% by weight of active ingredients.

6. The composition of claim 1, wherein the amount of Coenzyme-Q10 comprises about 15% mg by weight of active ingredients, the amount of red yeast rice comprises about 42.5% by weight of active ingredients, and the amount of phytosterols comprise about 42.5% by weight of active ingredients.

7. The composition of claim 1 further comprising inactive ingredients comprising at least one or more from the group consisting of dicalcium phosphate, microcrystalline cellulose, stearic acid, croscarmellose sodium, magnesium trisillicate, magnesium stearate, or hydroxypropyl methylcellulose.

8. The composition of claim 1 further comprising inactive ingredients comprising one or more spices.

9. The composition of claim 1 further comprising inactive ingredients comprising one or more emulsifiers.

10. The composition of claim 9, wherein the one or more emulsifiers comprising at least of lecithin, mono-n dye-glycerides, or combinations thereof.

11. The composition of claim 1, wherein the form of composition is selected from the group consisting of a pill, a tablet, a caplet, a capsule, powder, a suspension, and a gel.

12. The composition of claim 11 further comprising inactive ingredients comprising at least one carrier selected from the group consisting of water, milk, juice, soda, starch, vegetable oil, salt solution, hydroxymethyl cellulose, and carbohydrates.

13. A method for maintaining cardiovascular health comprising:
   administering a predetermined dosage of a composition for cardiovascular support comprising active ingredients consisting of:
   red yeast rice;
   Coenzyme-Q10; and
   phytosterols.

14. The method of claim 13, wherein the predefined dosage is administered over a predetermined time interval.

15. A composition for cardiovascular support comprising:
   active ingredients consisting of:
      about 10 mg to about 450 mg of Coenzyme-Q10;
      about 100 mg to about 2400 mg of red yeast rice; and
      about 100 mg to about 2400 mg of phytosterols;
   inactive ingredients comprising at least one or more excipients; and
   wherein the form of the composition is selected from the group consisting of a pill, a tablet, a caplet, a capsule, powder, a suspension, and a gel.

16. A composition for cardiovascular support comprising:
   active ingredients consisting of:
      about 10 mg to about 450 mg of Coenzyme-Q10;
      about 100 mg to about 2400 mg of red yeast rice;
      about 100 mg to about 2400 mg of phytosterols; and
      Omega-3 fish oil.

17. The composition of claim 15 wherein the inactive ingredients further comprise at least one or more from the group consisting of dicalcium phosphate, microcrystalline cellulose, stearic acid, croscarmellose sodium, magnesium trisillicate, magnesium stearate, or hydroxypropyl methylcellulose.

18. The composition of claim 15 wherein the inactive ingredients further comprise one or more emulsifiers, wherein the one or more emulsifiers comprising at least of lecithin, mono-n dye-glycerides, or combinations thereof.

19. The composition of claim 15 wherein the inactive ingredients further comprise at least one carrier selected from the group consisting of water, milk, juice, soda, starch, vegetable oil, salt solution, hydroxymethyl cellulose, or carbohydrates.

* * * * *